(12) United States Patent
Tang et al.

(10) Patent No.: US 9,027,431 B2
(45) Date of Patent: May 12, 2015

(54) REMOTE CENTRE OF MOTION POSITIONER

(75) Inventors: Hsiao-Wei Tang, Heverlee (BE); Hendrik Van Brussel, Kessel-lo (BE); Jan Peirs, Oud Heverlee (BE); Thierry Janssens, Meerbeek (BE)

(73) Assignee: Katholieke Universiteit Leuven, Leuven (BE)

( * ) Notice: Subject to any disclaimer, the term of this patent is extended or adjusted under 35 U.S.C. 154(b) by 570 days.

(21) Appl. No.: 13/320,582

(22) PCT Filed: May 12, 2010

(86) PCT No.: PCT/EP2010/056611
§ 371 (c)(1),
(2), (4) Date: Jan. 25, 2012

(87) PCT Pub. No.: WO2010/130817
PCT Pub. Date: Nov. 18, 2010

(65) Prior Publication Data
US 2012/0132018 A1    May 31, 2012

Related U.S. Application Data (60) Provisional application No. 61/216,276, filed on May 15, 2009.

(30) Foreign Application Priority Data

May 15, 2009 (GB) .................................. 0908368.4

(51) Int. Cl.
*B25J 17/00* (2006.01)
*A61B 19/00* (2006.01)

(52) U.S. Cl.
CPC ............. *A61B 19/22* (2013.01); *A61B 19/2203* (2013.01); *A61B 2019/2242* (2013.01); *A61B 2019/265* (2013.01); *Y10S 901/15* (2013.01); *Y10S 901/16* (2013.01); *Y10S 901/21* (2013.01)

(58) Field of Classification Search
USPC ............... 74/490.01–490.04, 490.08, 490.09; 901/15, 16, 21; 606/1, 130
See application file for complete search history.

(56) References Cited

U.S. PATENT DOCUMENTS 5,397,323 A * 3/1995 Taylor et al. .................. 606/130
(Continued)

FOREIGN PATENT DOCUMENTS

| EP | 0595291 A1 | 5/1994 |
| WO | 01/34017 A2 | 5/2001 |

OTHER PUBLICATIONS

International Search Authority/European Patent Office (ISA/EP). International Search Report and Written Opinion, Application No. PCT/EP2010/056611. Aug. 6, 2010.
(Continued)

*Primary Examiner* — David M Fenstermacher
*Assistant Examiner* — Emily Cheng
(74) *Attorney, Agent, or Firm* — The Marbury Law Group, PLLC (57) ABSTRACT

An apparatus having a member that revolves about a remote center of motion (RCM) and a base link coupled to a mounting fixture. A first and second link are pivotably coupled to the member at respective distances from the RCM and are translatable relative to the base link along a first direction, at a fixed ratio of displacement. The ratio of respective distances equals a fixed ratio of displacement. The apparatus has a translational motion generator for a first and second element along parallel opposing directions. The translational motion generator is disposed on the first link and enables motion parallel to the first direction. The base link is fixed in position, the first element is fixed to the base link and the second element is fixed to the second link, such that the first and second link may translate relative to the base link with fixed ratio of displacement.

19 Claims, 4 Drawing Sheets

(56) References Cited

U.S. PATENT DOCUMENTS

| | | | |
|---|---|---|---|
| 5,766,126 A | 6/1998 | Anderson | |
| 5,800,423 A * | 9/1998 | Jensen | 606/1 |
| 5,817,084 A * | 10/1998 | Jensen | 606/1 |
| 5,824,007 A | 10/1998 | Faraz et al. | |
| 6,246,200 B1 | 6/2001 | Blumenkranz et al. | |
| 6,702,805 B1 | 3/2004 | Stuart | |
| 6,723,106 B1 * | 4/2004 | Charles et al. | 606/130 |
| 7,021,173 B2 | 4/2006 | Stoianovici et al. | |
| 7,108,688 B2 * | 9/2006 | Jensen | 606/1 |

OTHER PUBLICATIONS

International Preliminary Examining Authority/European Patent Office (IPEA/EP). International Preliminary Report on Patentability, Application No. PCT/EP2010/056611. May 12, 2011.

* cited by examiner

REMOTE CENTRE OF MOTION POSITIONER

RELATED APPLICATIONS

This application is a U.S. national phase entry under 35 U.S.C. §371 of PCT Application PCT/EP2010/056611, which claims priority to United Kingdom Application 0908368.4, filed May 15, 2009, and U.S. Provisional Application 61/216,276, filed May 15, 2009.

FIELD OF THE INVENTION

This invention is related to the field of robotics, in particular to robot assisted surgery.

The present invention is directed to a remote centre of motion positioner used to support an instrument and provide a motion with fixed centre of rotation in a designated position where no physical object is present. It is very useful in performing robot assisted Minimally Invasive Surgery (MIS) to allow steering the surgical instrument inside a patient's body through a small incision on the patient's body.

STATE OF THE ART

In MIS procedure, a few small incisions (dia. 10 mm) are opened on a patient to allow instruments to be inserted therein. In one of the incisions, a laparoscope acquires the images inside the surgical site and shows it on a TV screen. Several other MIS instruments such as graspers, scissors, scalpel, and needle holders are inserted into the rest incisions. In order to be able to work through the small incision, these MIS instruments are often thin and long with at one end tools working in the surgical field and at the other end handles manipulated by a surgeon. The MIS techniques are different and more difficult compared with traditional open surgery. First of all, from a dexterity point of view, the motion of the surgeon's hand is constrained from 6 degrees of freedom (DOF) to 4 DOF. In addition to that, the small incision can be considered as the fulcrum of a lever. The scaling of the motion is not easy to be predicted by a novice surgeon. Secondly, the vision perception is degraded from 3 dimensions to 2 dimensions due to the imaging system. Therefore, to perform MIS surgical techniques a surgeon is demanded for additional training and practice in a limited number of simple procedures only.

Although the imposed difficulty troubles the surgeon, patients are taking much more advantages from the MIS procedures. Small incision means fewer traumas, faster recovery and less risk.

A robotic system (daVinci® surgical system of Intuitive Surgical, Inc.) has been developed to assist surgeons in performing MIS procedure. Equipped with 3D vision and additional 4 DOF Endowrist®, it successfully restores the lost dexterity and the missing visual perception. It is until now the most successful MIS robotic system in technology and in business outcome.

The daVinci® surgical system can be further divided into four components: the Remote Centre of Motion (RCM) Arm; the manipulator positioning linkage; the exchangeable surgical instruments (3D laparoscope and Endowrist®) and the surgeon console. The RCM arm employs the famous double-parallelogram mechanism or similar to provide the remote centre of motion where the centre of rotation is physically constrained (U.S. Pat. No. 7,108,688, U.S. Pat. No. 7,021,173, U.S. Pat. No. 5,397,323, U.S. Pat. No. 6,702,805). It decouples the two orthogonal rotational axes at the remote centre of motion, which can be directly controlled without the need of programming and complex inverse kinematics. The RCM arm allows the MIS instrument to be manipulated through the small incision with minimal stretching of the soft tissues. However, in order to obtain sufficient range of motion and stiffness, the resulting RCM arm employs a huge amount of working space above the patient. When two or more RCM arms cooperate to perform robotic MIS procedure, there is a great chance to hit the surgeon next to it or two arms will collide with each other during the manipulation. In addition, the physically fixed rotation centre requires additional manipulator positioning linkage (U.S. Pat. No. 6,246,200, U.S. Pat. No. 5,824,007) to align fixed remote centre to the small incision on the patient. It increases the cost and occupies significant space along the bedside. This prevents the surgeon to stay near the patient and to force him to perform his task on a surgeon's console which is located at a distance from the patient. In U.S. Pat. No. 7,108,688 and U.S. Pat. No. 5,397,323, a method to adjust the rotation point by adjusting the length of the linkages is proposed. However, the double-parallelogram mechanism will hang above the patient with only its one end supported by a revolute joint. This method will significantly reduce the stiffness and accuracy on the instrument holder and increases the size and weight of the whole arm.

Another mechanism which also provides a remote centre of motion is described in U.S. Pat. No. 5,766,126 and uses cross goniometric axes. The principal difficulty lies in the optimal choices between its size, payload, accuracy, and working radius. The patent derived manipulator Endoassist (Prosurgics Ltd, UK) employs a big structure to obtain sufficient range of motion. It occupies a bedside space and also a certain amount of working space above the patient. Not to mention the demand of high quality goniometric axes. Smaller manipulator examples like FIPS (Prototype of KARL STORZ GmbH & Co. KG, Germany), ViKY (Endocontrol Inc, France) and Freehand (Prosurgics Ltd, UK) are using small size goniometric axes. However, due to the mounting of the actuators and its mechanisms in the small area, their payload and range of motion are relatively small. On both big and small manipulators, due to their fixed remote centre of rotation, the adjustment of the remote centre point is obtained either by a mobile platform on the floor or a flexible arm (e.g. Fisso articulated arm, Baitella AG, Switzerland) coupled to the bed frame, which further increases the cost or decreases the stiffness.

In U.S. Pat. No. 6,723,106, a surgical manipulator is disclosed which employs a mechanism including two parallel arms pivotably supporting a medical tool with the orientation of the medical tool being adjusted by varying the position of joints. In order to achieve multiple degrees of freedom and adjust the remote centre of rotation via these two parallel arms, additional degrees of freedom are implemented, which couple the two orthogonal rotational axes at the remote centre of motion. The mechanism is not a passive remote centre of motion mechanism like the double parallelogram mechanism which means it requires dedicated programming and controller to execute its remote centre of motion.

In "A New, Compact MR-Compatible Surgical Manipulator for Minimally Invasive Liver Surgery", Medical Image Computing and Computer-Assisted Intervention—MICCAI 2002, pp. 99-106, Kim et al. disclose in FIG. 2 and FIG. 3 a remote centre of motion surgical manipulator comprising two parallel linkages pivotably connected to a gripper at fixed distances from the remote centre of motion. The two linkages are made to move linearly with fixed ratio so that the gripper is made to rotate about the remote centre of motion. The parallel linkages are driven by two ball screws. The two ball screws are coupled to a same motor through different gear transmission ratios, which provides for the fixed ratio linear motion of the parallel linkages.

In the latter RCM manipulator, the driving mechanism has a length equal to the total displacement of the linkages, which leads to a bulky arrangement and can lead to a lowered stiffness. Furthermore, the location of the remote centre of motion is only adjustable by using an adjustable mounting fixture which further affects the stiffness of the manipulator. The same drawbacks also apply as described above.

SUMMARY OF THE INVENTION

It is an aim of the present invention to provide an apparatus for generating motion around a remote centre of motion which makes it possible to solve the problems of the state of the art. In particular, it is an aim of the present invention to provide an apparatus having a remote centre of motion, which is more compact and has an increased stiffness compared to the RCM apparatuses of the prior art.

The invention provides for an apparatus, as set out in the appended claims, for generating motion around a remote centre of (rotary) motion, such as a manipulator or robot arm. The apparatus comprises a member arranged to revolve about the remote centre of motion, a base link coupled to a mounting fixture, and a first link and a second link arranged at a distance from each other. The first and second links are translatable relative to the base link, relative to each other and parallel to each other along a first direction, such that translational displacement of the first link relative to the base link and of the second link relative to the base link along the first direction occurs at a fixed ratio of displacement. The fixed ratio of displacement is such that the translational displacement of the first link is smaller than the translational displacement of the second link. The first link and the second link are pivotably coupled to the member at respective distances from the remote centre of motion, such that the ratio of said respective distances equals said fixed ratio of displacement. This constraint enables the member to revolve about the remote centre of motion.

According to the invention, the apparatus comprises means for generating (relative) translational motion of a first element and of a second element along parallel but opposite directions. Hence, said translational motion is such that the sense of (relative) displacement of the first element is opposite to the sense of (relative) displacement of the second element. The means for generating translational motion is provided on (or fixedly connected to) the first link and is so arranged (aligned) as to provide motion parallel to the first direction. By fixating the base link and providing the first element to be fixedly connectable to the base link and the second element to be fixedly connectable to the second link, it is obtained that generation of said translational motion of the first element and of the second element enables the first link and the second link to translate relative to the base link with said fixed ratio of displacement.

The present invention therefore proposes an alternative solution to the driving system of the linkage mechanism providing for a remote centre of motion. According to the invention, means are provided for generating two linear motions which are parallel, but of opposite sense. This means is provided on the movable link that has the smaller displacement. Hence, the motion generating means translates together with the first link. By fixing one linear motion to the fixed link (base link) and the other one to the movable link having the larger displacement, a driving mechanism is obtained that has a resemblance to a cascade system, in which the movable links can be displaced according to a predetermined ratio of displacement, relative to the base link.

An advantage of such a system is that the stroke of the driving mechanism need only be a fraction of the largest displacement achieved by the driven linkages. It follows that both a more compact, and stiffer manipulator can be obtained, which at the same time is easier and less costly to manufacture.

Preferably, the means for generating translational motion of the first element and of the second element is arranged to generate equal but opposite displacement of the first and second elements, such that the fixed ratio of displacement is 1:2. Such an assembly leads to the most simple implementation of the driving mechanism according to the present invention.

Preferably, the base link extends between the mounting fixture and the first element over a length which is adjustable along the first direction, which allows to adjust the location of the remote centre of motion along the first direction. An advantage of having the "cascade" driving system according to the present invention, is that the initial adjustment of the remote centre of motion along the first direction (direction of motion of the first and second links) is very simple to implement. It suffices namely to make the base link adjustable in length. Since the linkage mechanism formed by the first and second links and by the member are mounted on the base link, the stiffness of the system is not affected. Conversely, in the prior art RCM systems, making the remote centre of motion adjustable along the direction of motion of the manipulator arms always causes a stiffness decrease. More preferably, the adjustable length of the base link is obtained by providing a linear sliding element (a prismatic joint) dividing the base link in a first part that is connected to the mounting fixture and in a second part that is connected to the first element. Advantageously, the point of connection between the base link and the first link is provided on the first part. This allows to maintain the stiffness of the RCM arm, while providing for adjustment of the remote centre of motion along the first direction.

Preferably, the base link is coupled to the mounting fixture through a revolute joint having an axis of rotation parallel to the first parallel directions and comprising the remote centre of motion. As a result, an additional rotational DOF can be implemented for the member around the remote centre of motion.

Preferably, the means for generating translational motion comprises a pulley and belt mechanism, which is provided on the first link. The first and the second elements are provided on the belt. Alternatively, the means for generating translational motion comprises a roller element arranged to roll over two oppositely arranged rolling surfaces. The rolling surfaces form the first and the second elements. A preferred embodiment employs a pinion as roller element and a couple of racks a roller surfaces.

Preferably, the apparatus comprises a first linear sliding element (prismatic joint) between the base link and the first link and a second linear sliding element (prismatic joint) between the first link and the second link. The second link is hence coupled to the base link through the first link. Alternatively, the apparatus comprises a first linear sliding element between the base link and the first link and a second linear sliding element directly connected to the base link and to the second link. The linear sliding elements can act as bearing elements.

Preferably, the first link and the second link are coupled to the member by a revolute joint and a slide-revolute joint.

Preferably, the member is arranged as an instrument holder.

According to an aspect of the invention, an apparatus is provided comprising the following elements:
- a base link;
- a first and a second link whereby the first link is connected to the base link by a first prismatic joint, and the second link is connected to the first link by a second prismatic joint, and whereby the movement axes of the first prismatic joint and the second prismatic joint are parallel;
- an instrument holder supported by the first link with a revolute joint and by the second link with a slide-revolute joint; whereby the line between the revolute joint and the slide-revolute joint is intersecting with the movement axes of the first prismatic joint and the second prismatic joint and whereby the remote centre of motion is on said line and the revolute joint is proximal to the remote centre of motion while the slide-revolute joint is distal to the remote centre of motion; and
- a system for arranging a fixed displacement ratio between the second prismatic joint and the first prismatic joint whereby the displacement ratio is equal to the ratio between the distance between the remote centre of motion and the slide revolute joint and the distance between the remote centre of motion and the revolute joint.

An alternative embodiment is that the revolute joint is replaced by a slide-revolute joint and that the slide-revolute joint is replaced by a revolute joint. A sliding function should be implemented on at least one of the joints between the instrument holder and the first and second links.

In a preferred embodiment the system for arranging the fixed displacement ratio between the second prismatic joint and the first prismatic joint is a pulley system. In another preferred embodiment the displacement ratio is 1:2 and the pulley system comprises two pulleys (or sprockets) and a closed timing belt for circulating the pulleys whereby the pulley system is attached to the first link and whereby the line between the two rotational axes of the pulleys is parallel to the movement axis of the first prismatic joint and whereby one side of the closed timing belt is coupled to the base link and the other side of the belt is coupled to the second link. The closed timing belt can alternatively be a belt, wire, chain or cable or the like. The pulleys on the pulley system can alternatively be sprockets or similar devices with the same functionality.

In a preferred embodiment the apparatus of the present invention further comprises an additional link to the base link. Said additional link is connected to the base link by a third prismatic joint and is connected to the system for providing a fixed displacement ratio between the second prismatic joint and the first prismatic joint whereby the movement axis of the third prismatic joint is parallel to the movement axis of the first prismatic joint which allows for moving (adjusting) the remote centre of motion in the direction of the movement axes of the third prismatic joint and the first prismatic joint.

In yet another preferred embodiment the system for providing a fixed displacement ratio between the second prismatic joint and the first prismatic joint is a pulley system comprising two pulleys and the additional link is connected to the closed timing belt of the pulley system whereby the movement axis of the third prismatic joint is parallel to the movement axis of the first prismatic joint which allows for moving (adjusting) the remote centre of motion in the direction of the movement axes of the third prismatic joint and the first prismatic joint. Hereby, the adjustment of the remote centre of rotation in the direction of the movement axes of first and third prismatic joints is achieved by simultaneous and equivalent movement in said prismatic joints. The remote centre of motion can still be performed by fixing the motion on the third prismatic joint and is achieved by the pulley system and the first prismatic joint and the second prismatic joint.

In one embodiment, the apparatus of the present invention further comprises a third revolute joint connected to the base link for rotating the apparatus around an axis which is parallel to the first prismatic joint and intersects the remote centre of motion.

In another preferred embodiment the apparatus of the present invention further comprises an adjustment positioner for moving the apparatus in a plane which is perpendicular to the axis of the third revolute joint.

According to another aspect of the invention, an apparatus is provided comprising the following elements:
- a base link;
- a first and a second link whereby the first link is connected to the base link by a first prismatic joint, and the second link is connected to the first link by a second prismatic joint, and whereby the movement axes of the first prismatic joint and the second prismatic joint are parallel;
- an instrument holder supported by the first link with a revolute joint and by the second link with a slide-revolute joint (hereby the revolute joint can as well be a slide-revolute joint while the slide revolute joint is a revolute joint); whereby the line between the revolute joint and the slide-revolute joint is intersecting with the movement axes of the first prismatic joint and the second prismatic joint and whereby the remote centre of motion is on said line and the revolute joint is proximal to the remote centre of motion while the slide-revolute joint is distal thereto;
- a pulley system for arranging a fixed displacement ratio between the second prismatic joint and the first prismatic joint whereby the displacement ratio is equal to the ratio between the distance between the remote centre of motion and the slide revolute joint and the distance between the remote centre of motion and the revolute joint. The pulley system comprises two pulleys and a closed timing belt for circulating the pulleys whereby the pulley system is attached to the first link and whereby the line between the two rotational axes of the pulleys is parallel to the movement axis of the first prismatic joint;
- an additional link, said additional link connected to the base link by a third prismatic joint and said additional link coupled to one side of the closed timing belt of the pulley system, whereby the movement axis of the third prismatic joint is parallel to the movement axis of the first prismatic joint which allows for moving the remote centre of motion in the direction of the movement axes of the third prismatic joint and the second prismatic joint. Hereby the other side of the closed timing belt of the pulley system is coupled to the second link.

The adjustment of the remote centre of rotation in the direction of the movement axes of the first and third prismatic joints in the apparatus described above is achieved by simultaneous and equivalent movement in the first prismatic joint and the third prismatic joint. The remote centre of motion is performed by fixing the motion on the third prismatic joint and is achieved by the pulley system and the first prismatic joint and the second prismatic joint. In a preferred embodiment the displacement ratio is equal to 1:2 and when the third prismatic joint is fixed, a displacement of the first prismatic joint causes through the constraints on the pulley system a twice as large displacement of the second prismatic joint thereby producing the remote centre of revolute motion (since the distance between the centre of motion and the revolute joint is half of the distance between the centre of motion and the slide-revolute joint).

In one embodiment the apparatus of the present invention can further comprise a third revolute joint connected to the base link for rotating the apparatus around an axis which is parallel to the first prismatic joint and intersects the remote centre of motion.

In another preferred embodiment the apparatus of the present invention can further comprise an adjustment positioner for moving the apparatus in a plane which is perpendicular to the axis of the third revolute joint.

DETAILED DESCRIPTION OF THE INVENTION

Definitions

A "revolute joint" is a one degree of freedom kinematic pair which provides single axis rotation function.
A "prismatic joint" is a one degree of freedom kinematic pair which provides single axis linear motion capability.
"Movement axis of prismatic joint" is the line which coincides with the occurred motion of the kinematic pair of the prismatic joint
A "slide-revolute joint" is a two degrees of freedom joint which provides one degree of freedom rotation function along an axis of linear motion (one degree of freedom translation).
A "rigid link or link" is a solid object which connects with another rigid link via related joints to obtain relative motion.
A "belt clamp" is a physical fixation between the related link to the belt.

In a broad aspect an apparatus is provided for holding and manipulating an instrument about a predetermined remote centre of motion (rotation), which remains fixed during a given time period.

Figure 1:
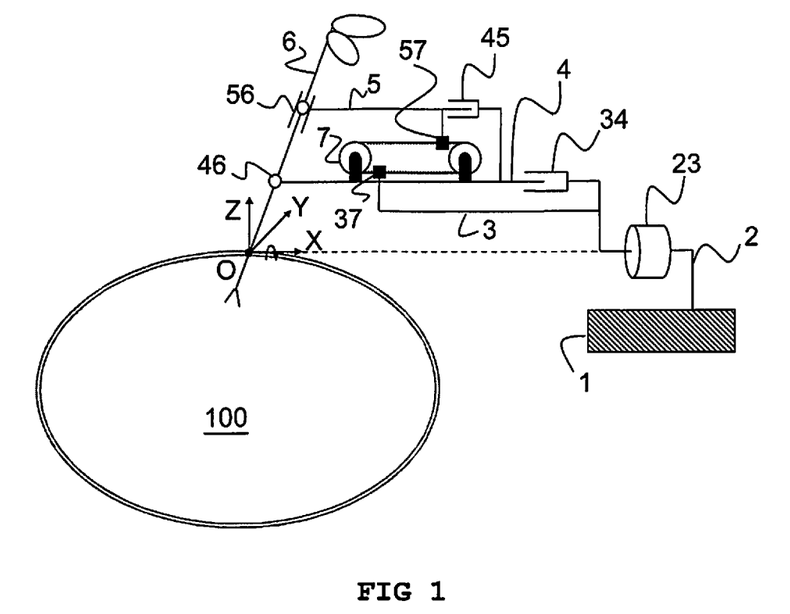
FIG. 1 shows an embodiment of the remote centre of motion mechanism.

An exemplifying embodiment of an apparatus according to the present invention is described in what follows, with reference to FIG. 1. The apparatus has a number of revolute and prismatic joints, rigid links and a constraint system to define the remote centre of motion. Preferably, the remote centre of motion (rotation) can be additionally adjusted. The apparatus can be either fixed on a frame 2, such as the bed frame, or on a mobile platform. The apparatus can be divided into a RCM mechanism and an adjustment positioner. The RCM mechanism has a base link preferably connected to a revolute joint the rotational axis of which coincides with the X-axis, which can revolve the whole RCM mechanism about the remote centre of rotation. This is a first rotational degree of freedom for the demanded remote centre of motion, but not the main one. The RCM mechanism, which provides a second rotational degree of freedom has several rigid links and joints. Two parallel links are connected by a prismatic joint. The first link of the parallel links is connected to the distal end of the base link with another prismatic joint. The two prismatic joints are also parallel in their motion. The two parallel links hold the instrument holder via one revolute joint and one slide-revolute joint. The axial direction of the instrument holder, which is inline from one joint to another, is intersecting with the remote centre of rotation. The parallel links, the instrument holder and base link constitute a plane and has a side intersecting with X-axis. This plane will rotate along the X-axis when rotating the revolute joint. To achieve the second degree of freedom, the ratio of the distances between the remote centre of rotation to the first joint and the second joint on the instrument holder is equal to the displacement ratio of the two parallel links. In this embodiment, a 1:2 displacement ratio is defined for the two parallel links via the constraint of the pulley system on it. The pulley system is implemented on the first link of the parallel link. The second link couples one side of the belt. The base link couples to the other side. Therefore, when propelling the belt on the pulley system, the transmission induces the same displacement of second link and base link at opposite direction. This enables the two parallel links (first and second links) to achieve 1:2 displacements. Thus, the instrument holder is placed at the distal part of the parallel links and is connected to the parallel links with a revolute joint and a slide-revolute joint. In this embodiment the distance from the remote centre of rotation to the first joint on the instrument holder is equal to the distance from the first joint to the second joint of rotation. Thus, the motion of the instrument holder is constrained to a rotation about the Y-axis. In this embodiment, the RCM mechanism physically constraints the instrument holder to rotate about two orthogonal axes and provides the remote centre of motion along a fixed position in space. This point of remote centre of rotation is a fixed position with respect to the RCM mechanism, which means its location has already been defined when constructing the mechanism.

To move the remote centre of rotation, which can be desired when implemented in the operating theatre, an adjustment positioner can be added to move the position in space. The adjustment positioner is designed with a traditional two degrees of freedom YZ table which is placed underneath the revolute joint to move the remote centre of rotation to its designated position in Y- and Z-axis.

To move the point along X-axis, an additional prismatic joint parallel to the parallel links is inserted between the belt clamp connecting the base link to the pulley system. In this way, the prismatic joint on the RCM mechanism is also employed to perform adjustment in X-axis. Unlike the traditional way of an additional link and prismatic joint which has to support and move the whole mechanism in X axis, the method in this embodiment preserves the original stiffness of the RCM mechanism but equips it with demanded adjustment functions.

Apparatuses according to the present invention can manipulate an instrument at a fixed rotation centre, which is physically defined by a RCM mechanism. Therefore, it can be used passively by opening/releasing the brakes or friction components and a user may manipulate the instrument in the instrument holder while the RCM mechanism constraints the point of rotation without the use of actuation. It can also be applied actively to implement motors and actuators on its links, joints and instrument holders to control the instrument to reach the desired position and orientation. It keeps the whole mechanism at a fixed distance to the patient which greatly reduces the risk of contacting the patient. It also minimizes the working space above the patient along its range of motion which allows co-manipulation with surgeons and multiple arms cooperation at the same time without colliding with each other.

The apparatus preferably further employs a technique which enables the adjustment of the remote centre of rotation by adjusting the position of the belt clamp rather than by adjusting the whole mechanism. Because the belt clamp is not a structure component, it can be design embedded onto the existing linkage which reduces the weight and cost and maintains the stiffness of the whole structure.

FIG. 1 shows an embodiment of the remote centre of motion mechanism according to the invention in a typical application of MIS on a patient 100. A base link 3 is connected to one side of the revolute joint 23. The rotational axis of joint 23 is placed in line with the X-axis of the XYZ coordinate, which its origin O coincides with the small incision on the patient. It is also the remote centre of rotation for the surgical instrument that enters and is manipulated inside the body by levering on the point O. Revolute joint 23 provides one degree of freedom of rotating along X-axis and is connected via a link 2 to a mounting fixture 1.

A first link 4 has three joints. The first link 4 connects to the base link 3 with prismatic joint 34. The first link 4 connects to the second link 5 with prismatic joint 45. The prismatic joint 34 and prismatic joint 45 are parallel to X-axis and are intersecting with the instrument holder 6. A pulley system 7, which is composed by two pulleys and a closed timing belt or cable or wire circulating the pulleys, is attached on the first link 4. The line between the two rotating axes of the pulleys is parallel to the direction of prismatic joint 34 and prismatic joint 45. On one side of the belt, a belt clamp 37 is fixed to the base link 3. On the other side, belt clamp 57 is fixed to the second link 5. Since the pulleys are freely rotating each around its axis, the first link 4 can have a linear displacement via the prismatic joint 34. It will also drive the belt to propel on pulley systems 7 due to the fixed belt clamp 37 and cause the second link 5 to slide via the prismatic joint 45. Thus, the displacement ratio of the prismatic joint 34 and prismatic joint 45 with respect to base link 3 will be 1:2 due to the constraint of the pulley system 7. The instrument holder 6 is supported by the first link 4 with a revolute joint 46 and by the second link 5 with a slide-revolute joint 56. The revolute joint 46 is nearer the remote centre of rotation compared to slide-revolute joint 56. The line connecting joint 46 and joint 56 is intersecting with the remote centre of rotation. The distance between O to joint 46 is equal to the distance between joint 46 and joint 56. A surgical instrument which is inline with the line connecting joint 46 and joint 56 is held by the instrument holder and inserted into the small incision on the patient 100. Thus, the orientation of the surgical instrument is steered by the revolute joint 23 to obtain its rotation around X-axis. The displacements of the joint 46 and joint 56, which are the identical to the motion on the prismatic joint 34 and 45, will provide the surgical instrument to rotate around Y-axis.

Figure 2:
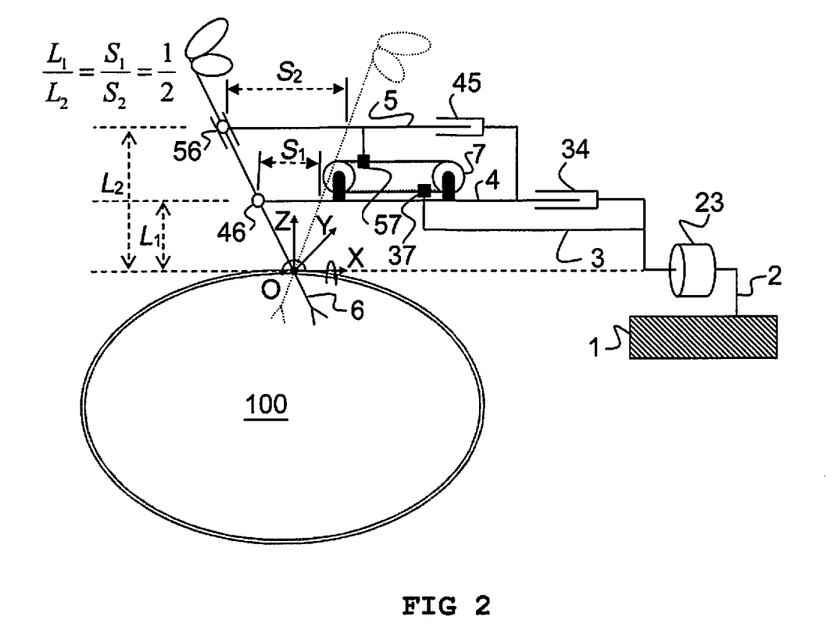
FIG. 2 shows the system of FIG. 1 wherein the instrument holder is rotated around the remote centre of motion. The constraints for a 1:2 ratio displacements on parallel links to provide the remote centre of motion in Y-axis is represented as well.

FIG. 2 shows the pulley system 7 constraints with the 1:2 ratio displacements on parallel links 4 and 5 to provide remote centre of motion around Y-axis. A surgical instrument is held by the instrument holder 6 and inserted into the small incision O on patient 100. The distance L1 is the vertical distance (in Z-direction) from point O to joint 46. The distance L2 is the vertical distance from point O to joint 56. Thus, L1:L2=1:2 since the distance from point O to joint 46 is equal to joint 46 to joint 56. S1 is the displacement along X-axis of the joint 46 with respect to base link 3 via the motion on prismatic joint 34. S2 is the displacement along X-axis of joint 56 with respect to base link 3 via the motion on prismatic joint 45. Due to the variable distance between joint 45 and joint 56 with respect to their motions, a sliding function is implemented on joint 56. An alternative is to put the sliding function on joint 46. Since the pulley system 7 is connected via belt clamp 37 to the base link 3 and via belt clamp 57 to the second link 5, S1 and S2 have a fixed ratio of 1:2. Therefore, the instrument holder 6 always points toward the vertex O of the triangles, which are formed by the span of surgical instrument and the trajectories of the joint 46 and joint 56. By appropriate selecting the distance L1 and the demanded range of rotation in Y-axis, the remote centre of motion can provide a minimum profile of its working space above the patient and keep the RCM mechanism at a constant distance (L1) to the patient. This is advantageous compared to the remote centre of motion generated by a double parallelogram mechanism, wherein the rotation about the remote centre of motion (on Y-axis) is the result of the two coupled parallelograms manipulating the instrument holder above the patient. The distance to the patient and the working space above the patient are varying based on the angle of the instrument holder. This increases the possibility of colliding with the patient and also with other robot arms.

Figure 7:
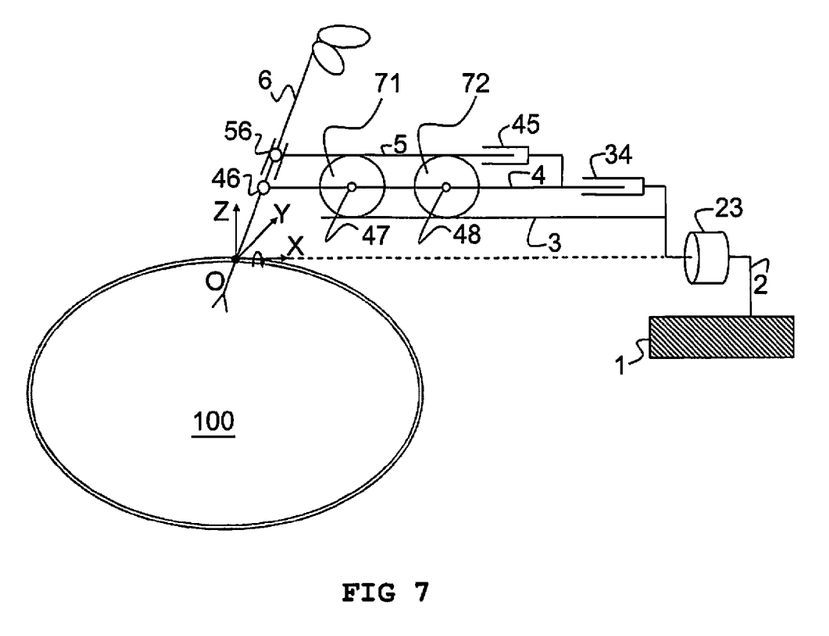
FIG. 7 shows an alternative scheme of the mechanism for obtaining a 1:2 ratio displacement between two parallel translating links, based on one or more roller elements.

The pulley and belt system described above, can be replaced by one or more roller elements as shown in FIG. 7. FIG. 7 shows the mechanism for obtaining a 1:2 ratio displacement between two parallel translating links. First link 4 and second link 5 slide in linear bearing elements (prismatic joints) 34 and 45 respectively. Between the second link 5 and the base link 3 roller elements 71 and 72 are provided which are constrained to roll without slipping on rolling surfaces provided on second link 5 and base link 3 respectively. This constraint can be achieved by the use of high friction materials with preloading, by zero-backlash rack-and-pinion elements, or by any suitable means known in the state-of-the-art. First link 4 is connected to the centre of the rolling elements 71 and 72 by revolute joint 47 and 48 respectively. The roller elements 71 and 72 constraints the 1:2 ratio displacements on parallel links 4 and 5 to provide remote centre of motion on Y-axis.

The two rolling elements 71 and 72 can be replaced by a single rolling element if the linear bearing elements 34 and 45 take care of the parallelism between first link 4 and second link 5.

Figure 3:
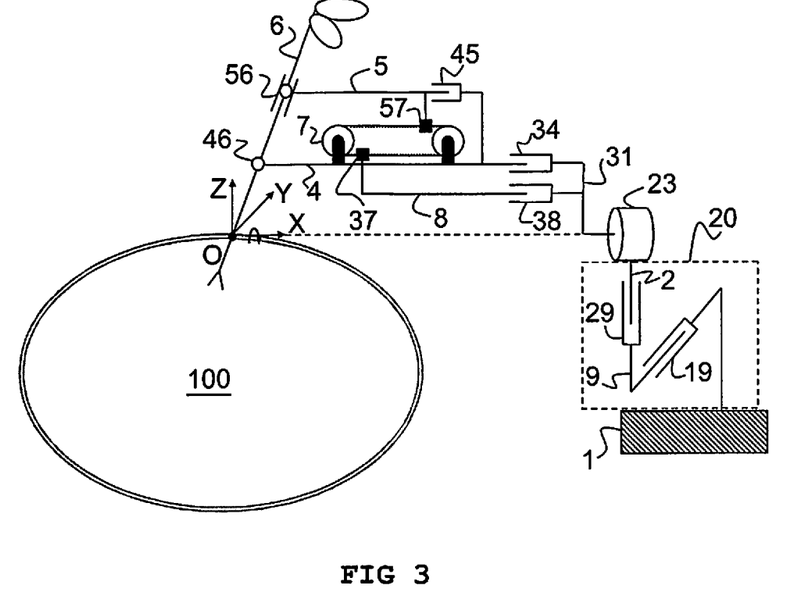
FIG. 3 shows an embodiment of the remote centre of motion mechanism and adjustment positioner.

FIG. 3 shows an embodiment of an adjustable remote centre of motion mechanism. The RCM mechanism of FIG. 1 is connected to one side of the revolute joint 23 whose rotational axis is in line with the X-axis. An adjustment positioner is composed by an YZ table 20 and an additional prismatic joint 38 between the belt clamp 37 and base link 3. The YZ table 20 is connected to the other side of the revolute joint 23 and comprises a prismatic joint 29 for moving the whole RCM mechanism in Z direction and a prismatic joint 19 for moving the whole RCM mechanism, the connecting link 2, link 9 and prismatic joint 29 along Y direction. The remote centre of rotation O can be adjusted via the YZ table 20.

As a general rule the more adjustment degrees of freedom are implemented, the heavier and stronger the adjustment devices need to be in order to preserve the stiffness of the system. According to an aspect of the present invention, a different approach is implemented for adjusting the remote centre of rotation O in X-direction, which avoids the above problems. An additional prismatic joint 38 is provided on the base link, and which divides the base link into a link 31 connected to the mounting fixture 1 (through revolute joint 23 and YZ table 20) and a link 8 connected to the belt clamp 37. The prismatic joint 38 is parallel to joint 34 and connects link 31 and link 8. With this kind of arrangement, link 4, link 8 and link 5 can have relative movement against link 31 in X-direction. An adjustment of the remote centre of rotation O in X-direction is achieved by simultaneous and equivalent movement in prismatic joint 34 and prismatic joint 38. The motion of the instrument holder 6 around the remote centre of motion O can be still performed by fixing the motion on prismatic joint 38 and actuating the pulley system 7 to cause translational motion in joint 34 and joint 45. Since the belt clamp 37 only receives the load exerted on belt and does not support the whole RCM mechanism above it, the added prismatic joint 38 can be made small depending on the load on the belt clamp 37. The base link 31 is still the main component for the structure stiffness. This arrangement makes use of the prismatic joint 34 to not only provides remote centre motion together with prismatic joint 45 but also to give an added function to adjust the remote centre of rotation O together with prismatic joint 38.

Figure 4:
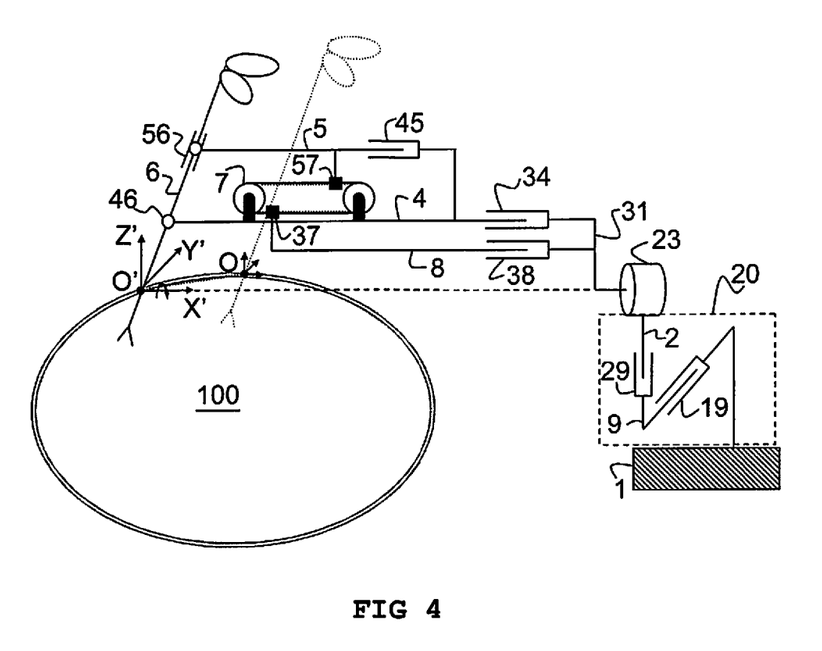
FIG. 4 shows the adjustment of the remoter centre of rotation from O to O' by adjusting the position of the belt coupling and YZ table.

FIG. 4 shows the adjustment of the remoter centre of rotation from O to O' by adjusting the position of the belt clamp 37 and YZ table. A surgical instrument is held by instrument holder 6 and is supported by the RCM mechanism on one side of the revolute joint 23. The remote centre of rotation will be shifted from point O to point O'. Thus, the YZ table connected to the other side of the revolute joint 23 makes the adjustment of its respective Y and Z directions. The prismatic joint 34 and prismatic joint 38 move together while the prismatic joint 45 keeps static to perform the adjustment of the remote centre of rotation in X-direction. The pulley system 7 is not propelled during the adjustment period. When the adjustment is completed, RCM is enabled when the prismatic joint 38 is fixed. The orientation of the surgical instrument is steered by the revolute joint 23 to obtain its rotation around X-axis. The displacements of the joint 46 and joint 56, which are identical to the motion on the prismatic joint 34 and 45 while the prismatic joint 38 keeps static, will provide the surgical instrument to rotate around Y-axis.

Figure 5:
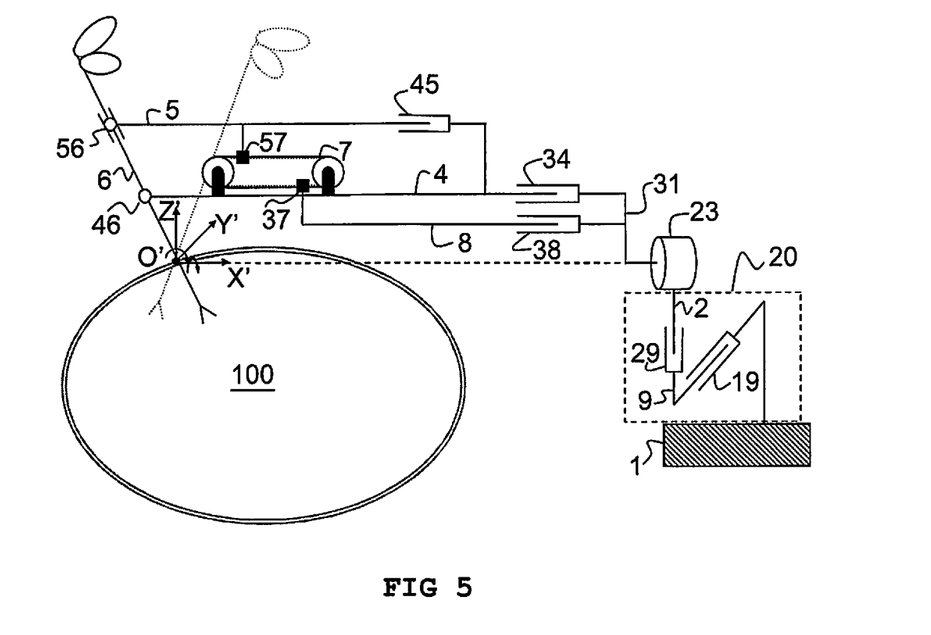
FIG. 5 shows motion about the remote centre of motion provided by the apparatus of FIG. 4 after adjusting the remote centre of motion.

FIG. 5 shows the remote centre of motion provided by the embodiment of FIG. 4 after adjusting the remote centre of rotation. The YZ table and the prismatic joint 38 keep static which enables the pulley system 7 to perform its 1:2 displacement constraints to joint 46 and joint 56. The instrument holder 6 always points toward the vertex O' of the triangles, which are formed by the span of instrument holder 6 and the trajectories of the joint 46 and joint 56.

Figure 6:
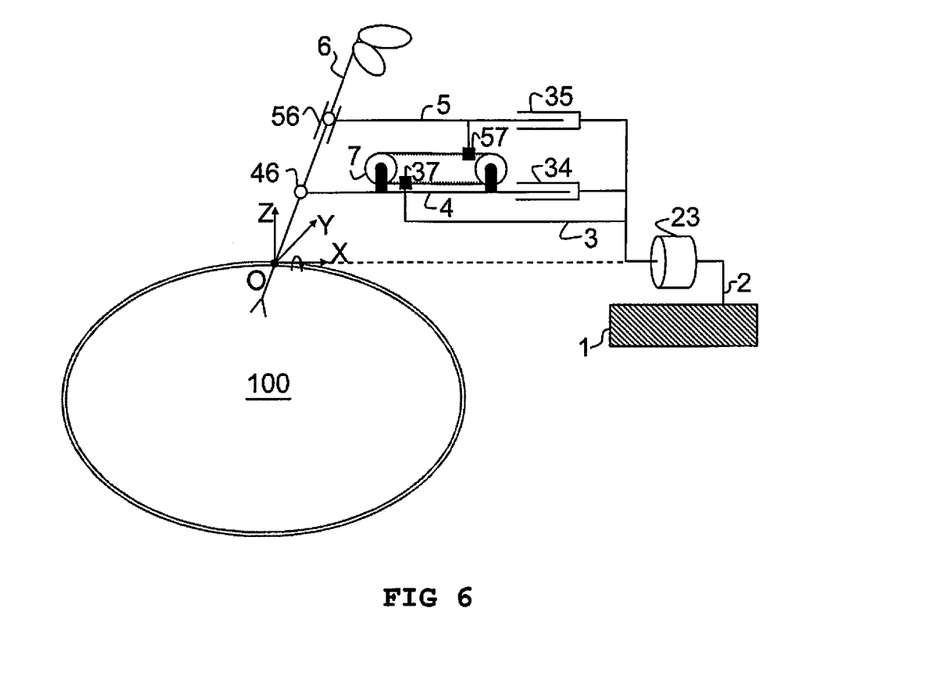
FIG. 6 shows an alternative embodiment of an apparatus according to the present invention, wherein the second link is directly attached to the base link through a prismatic joint.

FIG. 6 shows an alternative embodiment to the apparatus of FIG. 1. The second link 5 is connected to the base link 3 with the prismatic joint 35. The advantage of this alternative is the even distribution of the load on the prismatic joint 34 and 35. However, the drawback is that the stroke of prismatic joint 35 is twice the stroke of prismatic joint 34, whereas in the embodiment of FIG. 1, the prismatic joint 34 and 45 have the same stroke since the second link is connect to the first link.

The invention claimed is:

1. An apparatus for generating motion around a remote centre of rotary motion, comprising:
    a member arranged to revolve about the remote centre of motion;
    a base link adapted to be coupled to a mounting fixture;
    a first link and a second link arranged at a distance from each other and linearly translatable relative to the base link, relative to each other and parallel to each other along a first direction, such that a translational displacement of the first link relative to the base link and of the second link relative to the base link along the first direction occurs at a fixed ratio of displacement, said translational displacement of the first link being smaller than said translational displacement of the second link;
    wherein the first link is connected to the second link such that the first link and second link translate dependently in the first direction;
    wherein the first link and the second link are pivotably coupled to the member at respective distances from the remote centre of motion, such that the ratio of said respective distances equals said fixed ratio of displacement, enabling the member to revolve about the remote centre of motion; and
    a motion generator configured for generating translational motion of a first element and of a second element along parallel but opposite directions and parallel to the first direction, wherein the motion generator is fixedly secured to the first link to translate together with the first link such that when translational motion is generated the base link is fixed in a position, the first element is fixedly secured to the base link and the second element is fixedly secured to the second link, such that the motion generator enables the first link and the second link to translate relative to the base link with said fixed ratio of displacement.

2. The apparatus of claim 1, wherein the motion generator is arranged to generate equal but opposite displacement of the first and second elements, such that said fixed ratio of displacement is 1:2 between the first link and the second link with respect to the base link.

3. The apparatus of claim 2, wherein the base link has an adjustable length between the mounting fixture and the first element so as to adjust the location of the remote centre of motion.

4. The apparatus of claim 2, wherein the motion generator comprises a roller element arranged to roll over two oppositely arranged rolling surfaces forming the first and the second elements.

5. The apparatus of claim 4, wherein the roller element is a pinion and the rolling surfaces are racks.

6. The apparatus of claim 2, wherein the motion generator comprises a pulley and belt mechanism.

7. The apparatus of claim 1, wherein the base link has an adjustable length between the mounting fixture and the first element so as to adjust the location of the remote centre of motion.

8. The apparatus of claim 7, wherein the base link comprises a linear sliding element dividing the base link in a first part adapted to be coupled to the mounting fixture and a second part connected to the first element for making the length of the base link adjustable along the first direction and wherein the first part connects the base link and the first link.

9. The apparatus of claim 1, wherein the base link is adapted to be coupled to the mounting fixture through a revolute joint having an axis of rotation parallel to the first direction and the axis of rotation of the revolute joint comprising the remote centre of motion.

10. The apparatus of claim 1, wherein the motion generator comprises:
    a pulley and belt mechanism comprising an endless belt running over the pulley, such that two parts of the endless belt extend from the pulley at a same side of the pulley, wherein the two parts move along the parallel but opposite directions, wherein the first element is secured to the endless belt at one of the two parts and the second element is secured to the endless belt at the other one of the two parts.

11. The apparatus of claim 1, wherein the motion generator comprises a roller element arranged to roll over two oppositely arranged rolling surfaces forming the first and the second elements.

12. The apparatus of claim 11, wherein the roller element is a pinion and the rolling surfaces are racks.

13. The apparatus of claim 1, comprising:
a first linear sliding element between the base link and the first link; and
a second linear sliding element between the first link and the second link.

14. The apparatus of claim 13, wherein the linear sliding elements are prismatic joints.

15. The apparatus of claim 1, comprising:
a first linear sliding element between the base link and the first link; and
a second linear sliding element connecting the base link with the second link.

16. The apparatus of claim 1, wherein the first link and the second link are coupled to the member by a revolute joint and a slide-revolute joint.

17. The apparatus of claim 1, wherein the member is arranged as an instrument holder.

18. The apparatus of claim 1, wherein the motion generator is configured for generating linear motion.

19. The apparatus of claim 1, wherein during operation of the apparatus the base link, the first link and the second link are rigid links.

* * * * *